United States Patent [19]

Berrang et al.

[11] Patent Number: 6,074,422
[45] Date of Patent: Jun. 13, 2000

[54] INNER EAR IMPLANT DEVICE

[75] Inventors: Peter Berrang; Alan Lupin, both of Victoria, Canada

[73] Assignee: Epic Biosonics Inc., Victoria, Canada

[21] Appl. No.: 09/064,137

[22] Filed: Apr. 22, 1998

[51] Int. Cl.[7] .............................. A61F 2/18; A61N 1/04
[52] U.S. Cl. ............................................ 623/10; 607/137
[58] Field of Search ............................. 623/10; 128/784; 607/137

[56] References Cited

U.S. PATENT DOCUMENTS

| | | |
|---|---|---|
| 4,261,372 | 4/1981 | Hansen . |
| 4,762,135 | 8/1988 | van der Puije et al. . |
| 4,832,051 | 5/1989 | Jarvik et al. . |
| 5,123,422 | 6/1992 | Charvin . |
| 5,344,387 | 9/1994 | Lupin . |
| 5,545,219 | 8/1996 | Kuzma . |
| 5,578,084 | 11/1996 | Kuzma et al. . |
| 5,645,585 | 7/1997 | Kuzma . |
| 5,653,742 | 8/1997 | Parker et al. . |

OTHER PUBLICATIONS

"Cochlear Prostheses" by G.M. Clark et al., Churchhill Livingstone, New York, 1990, Ch.1, pp. 1–14.
"Dimensions of the Scala Timpani in the Human and Cat with Reference to Cochlear Implants" by S.Hatsushika. Ann. Otol. Rhinol. Laryngol. 99:1990, pp. 871–876.
"The Scala Vestibuli for Cochlear Implantation—An Anatomic Study" by A.J. Guyla et al, Arch Otolaryngol. Head Neck Surg., vol. 22, Feb. 1996, pp. 130–132.
"A Tantalum–on–Sapphire Microelectrode Array" by G.A. May et al. IEEE Transactions on Electron Devices, vol. ED–26 No. 12, Dec. 1979, pp. 1932–1939.

"A prototype flexible microelectrode array for implant–prosthesis applications" by M.Sonn et al. Medical and Biological Engineering, Nov. 1974, pp. 778–790.

*Primary Examiner*—Mickey Yu
*Assistant Examiner*—Choon P. Koh
*Attorney, Agent, or Firm*—Paul Smith Intellectual Property Law; Paul Smith

[57] ABSTRACT

A dual prong hearing prosthesis for surgical implantation into both the scala tympani and the scala vestibuli of the inner ear of deaf persons is presented. The prosthesis consists of two prongs each with a plurality of closely spaced electrodes at the proximal end, said electrodes configured to stimulate the auditory nerves of the inner ear at a plurality of sites. One prong carries circumferentially-configured electrodes while the electrodes of the other prong are longitudinally-configured in relation to the length of the prong. Conductor lines from each electrode on both prongs terminate at the distal end in a contact pad arrangement thereby enabling convenient electrical connection between the implant and speech processing electronics. Means are disclosed to minimize kinking of the prongs during implantation, and to enable the electrodes to be in close proximity to the modiolus and basilar membrane thereby allowing for a high degree of versatility in selecting discrete stimulation sites.

27 Claims, 8 Drawing Sheets

INNER EAR IMPLANT DEVICE

FIELD OF THE INVENTION

This invention relates to human auditory prostheses, and more specifically to an implant having a novel dual prong electrode array configuration for inner ear nerve stimulation, as well as a means to position the implant in the scala tympani and the scala vestibuli.

BACKGROUND OF THE INVENTION

The inner ear (or cochlea) is a small double channel helical-shaped feature in the skull containing a key part of the human hearing mechanism. Nerves are arranged in the center of the cochlea (modiolus) and branch out into the basilar membrane. This membrane separates the scala tympani channel on one side, and the combined scala vestibuli and scala media channels on the other side. Since the scala media adjoins the scala vestibuli via a very thin membrane, for convenience, both of these scalae are referred to herein as the scala vestibuli. Sound waves are collected by the external ear and transmitted to the tympanic membrane (or ear drum), which then transfers the vibrations to the fluid in the scala vestibuli via the three auditory ossicles in the middle ear. The acoustic waves in the scala vestibuli are further transmitted to the scala tympani via a small opening (the helicotrema) at the apical end of the cochlea. A resonance is set up in the two scalae whereby the acoustic waves in the scalae are out of phase with each other, thereby causing the thin basilar membrane separating the two scalae to oscillate. A complex arrangement of hair cells on the basilar membrane are activated by the movement of said membrane, which trigger a nerve response which is interpreted by the brain as speech.

One cause of profound deafness is the loss or destruction of hair cells within the cochlea. Without these hair cells, there is no tactile input to the auditory nerves. Although there is currently no method for replacing the hair cells, it has been demonstrated that the auditory nerves respond directly to electrical stimulation. This direct electrical stimulation of the auditory nerve in the cochlea is the basis of modern cochlear implants. A comprehensive introduction of the history of the development of cochlear implants is given by, for example, G. M. Clark, et. al., Chapter 1, pages 1–14, in Cochlear Prostheses, edited by G. M. Clark, Y. C. Tong and J. F. Patrick, distributed in the U.S.A. by Churchill Livingstone Inc., New York, N.Y. (ISBN 0-443-03582-2).

The current state of the art of electrode devices used in commercial cochlear implants consists of one or more electrodes on a single probe inserted into the scala tympani. The electrodes are electrically connected to an electronic package anchored in the mastoid bone behind the ear. An acoustic signal is received by a microphone located on an external body-mounted electronics package and, using a speech processing strategy, is converted for transmission, through the skin, to the unit anchored in the mastoid bone.

The electrodes are generally comprised of small platinum/iridium balls or circular platinum rings connected internally by thin wires, with the electrodes and wires held together by an inert silicone carrier. Various interconnection combinations between the electrodes on the single implant probe are used to create a map or stimulation pattern within the cochlea. To date, data from implanted patients indicate highly variable speech recognition results from patient to patient. The reason for this high variability is not known. In general, there is some suggestion that more electrodes can provide improved patient hearing percepts. Although implants with only one electrode have been successful, there is growing evidence that multi-electrode implants, especially combined with advanced speech processing technology, can provide superior speech understanding for the patient. However, there is no firm evidence as to the optimum number of electrodes, although there is some support for the notion that more electrodes is better. This technology is described in, for example, T. J. Balkany, editor of The Otolaryngologic Clinics of North America, Vol. 19, No. 2, May, 1986, titled The Cochlear Implant, (ISSN 0030-6665), and, more recently, in the Abstract Proceedings from the Conference on Implantable Auditory Prostheses, Aug. 17–21, 1997, held in Pacific Grove, Calif. U.S.A.

Many attempts have been made to design electrodes that can be positioned near the lateral walls of the scala tympani, especially near the modiolus. For example, Kuzma describes in U.S. Pat. Nos. 5,545,219 and 5,645,585 means for positioning a flexible rod-like carrier held by a positioning member to position the electrodes near the modiolus. In U.S. Pat. No. 5,578,084, Kuzma further describes a method for altering the shape of an electrode in situ through the use of bio-absorbing materials so as to position it closer to the medial wall of the cochlea. Parker et. al. details the use of bio-resorbable materials to allow an electrode to change shape after insertion in the cochlea in U.S. Pat. No. 5,653,742.

All cochlear electrode arrays to date have been developed for insertion into only the scala tympani. However, in some cases it is not possible to insert the electrodes into the scala tympani due to ossification. One option for the surgeon is to then attempt to implant the electrodes into the scala vestibuli. Evidence to date suggests that implantation of electrodes into the scala vestibuli results in similar hearing percepts by the patient compared to implants in the scala tympani (A. J. Gulya, et. al., Arch. Otolaryngo Head Neck Surg./Vol. 122, February 1996). Thus, it appears that from a medical perspective, implantation of an electrode array into either scala is viable.

No data are available on the implantation and use of electrode arrays in both scalae of the cochlea although it is interesting to note that Hansen in U.S. Pat. No. 4,261,372 describes the use of a two part electrode array where one part of the electrode array is inserted into the first turn of the scala tympani and the other part is inserted into the second turn of the scala tympani. This prior art is a single electrode array comprised of two parts, and configured to enter the same scala to obtain improved insertion depth of the electrode array.

Conventional single probe implants tend to be positioned near the lateral wall in the scala tympani, whereas the stimulatable spiral ganglion cells are located near the modiolus, resulting in high threshold currents, a lack of electric field discrimination and crosstalk effects. The nerve cells in such a configuration are simply too far away from the electrodes to be discretely stimulated.

In addition to nerve proximity, issues have arisen wherein the insertion of the device causes the array to twist, resulting in a non-optimal placement. It is believed that much of the variation in the performance of these electrode arrays results from the imperfect science of device insertion during surgery. Designs which preferentially turn in one plane while maintaining their rigidity in the other plane have been described in, for example, U.S. Pat. No. 5,123,422 and U.S. Pat. No. 4,832,051.

It is noted that the electrode array devices that have been disclosed suffer from a variety of limitations, which predispose them to meeting some criteria while not meeting others. The electrode array criteria that are generally believed to provide for optimum performance are: (1) electrode proximity to functional ganglion cells near the modiolus (i.e. the central core of the cochlea), (2) surgical insertability of the entire electrode array into the scala and (3) density of electrodes (number of electrodes per unit length).

The object of this invention is to provide an implant device that overcomes the limitations of the prior art, as well as a method of surgical implantation of such a device.

It is a further object of this invention to provide an implant which increases selectivity of stimulation sites, localizes the electric field distribution, minimizes the electrical stimulation current required, improves the ease of surgical implantation and positioning, and improves patient speech percepts.

SUMMARY OF THE INVENTION

The implant according to the invention is designed to allow the positioning of electrodes in both scalae.

The implant consists of two elongated prongs extending from a common base. Each of the prongs includes one or a plurality of electrodes. In the preferred embodiment, the electrodes on one prong are oriented longitudinally on the prong while those on the other prong are oriented transversely to the longitudinal axis of the prong. The implant is designed to enable one prong to be surgically implanted in the scala tympani while the other is implanted in the scala vestibuli and such surgical approach is an aspect of the invention. Prior to insertion, each of the prongs is rolled up about its longitudinal axis and the prongs are unrolled in situ.

The orthogonality between the circumferentially-configured electrodes in one scala and the longitudinally-configured electrodes in the other scala allows for electrical current to be applied over a large number of small discrete volumes to ascertain the optimum sites for stimulating the functional nerve cells in the basilar membrane and the ganglion cells near the modiolus.

Since the separation between electrodes in opposing scalae can be relatively small, thereby creating a highly localized electric field, relatively low electrical currents can be applied to said electrodes to stimulate discrete areas of functioning nerve cells. This close spacing between electrodes in different scalae somewhat reduces adjacent same scala electrode crosstalk, and thus allows for closer spacing between same scala electrodes.

Alternative embodiments of electrode arrangements on a dual prong implant device are to (1) orient the electrodes circumferentially on both prongs, and (2) orient the electrodes circumferentially on one prong and use a single electrode on the other prong which covers the entire cylindrical surface area, said electrode essentially acting as a ground plane within the scala. Either of these electrode embodiments would still provide increased selectivity of stimulation sites and reasonable stimulation threshold currents compared to conventional bipolar and monopolar electrode configurations.

Expansion of the implanted prongs to position said electrodes in closer proximity to the medial and lateral walls of the scalae is desirable, since it will tend to reduce threshold electrical currents and provide enhanced electrical field discrimination. Means to expand the rolled-up prongs of the present invention, in situ, can be conveniently accomplished using the naturally flexible nature of the prong's electrode material and or electrode-carrier material that will tend to un-coil, thus expanding the outside diameter of the rolled-up prong. This expansion means may be combined with, for example, the use of chemical expansion by hydroscopic core material present inside the rolled-up prong, which will gradually absorb fluid from the surrounding perilymph.

If it is determined during surgery that one scala is ossified, precluding insertion of both electrode prongs, the circumferentially-configured prong can be inserted into the other scala, and the longitudinally-configured prong simply cut away. This embodiment will still provide a functional hearing device for the patient, albeit at some degradation in speech percepts by the patient.

For hearing convenience, the present invention includes one embodiment whereby the microphone used to receive speech signals is mounted directly on or incorporated into the section of the implant device positioned in the middle ear. This arrangement will allow the patient to hear in a more natural way via the ear channel, rather than via an externally mounted microphone, which may be some distance away from the ear channel.

Other features of the invention are defined by the claims and will become apparent from the following detailed description of the preferred and alternative embodiments.

BRIEF DESCRIPTION OF DRAWINGS

The preferred and alternative embodiments of the invention will be described by reference to the accompanying drawings, in which.

DESCRIPTION OF PREFERRED EMBODIMENTS

Figure 1:
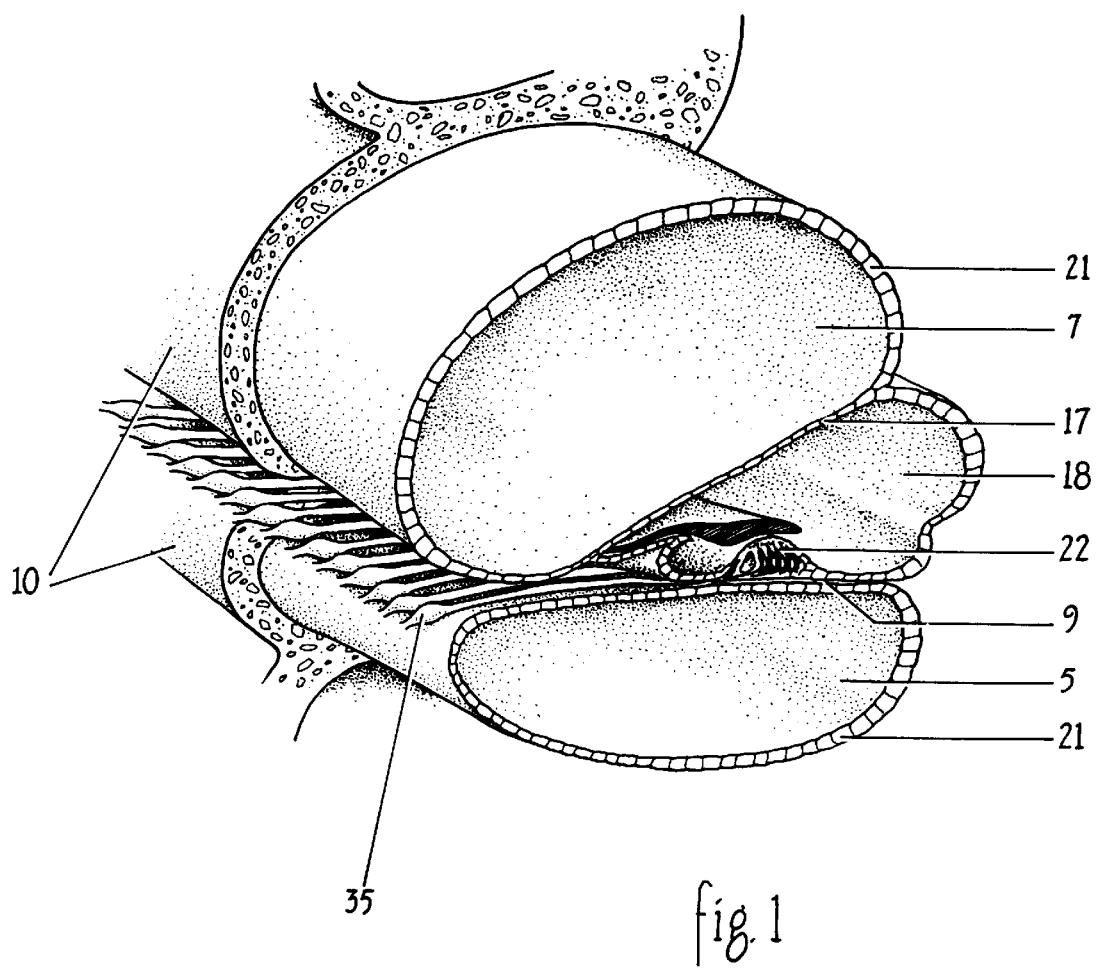
FIG. 1 is a cross sectional view of the scalae.
Figure 4:
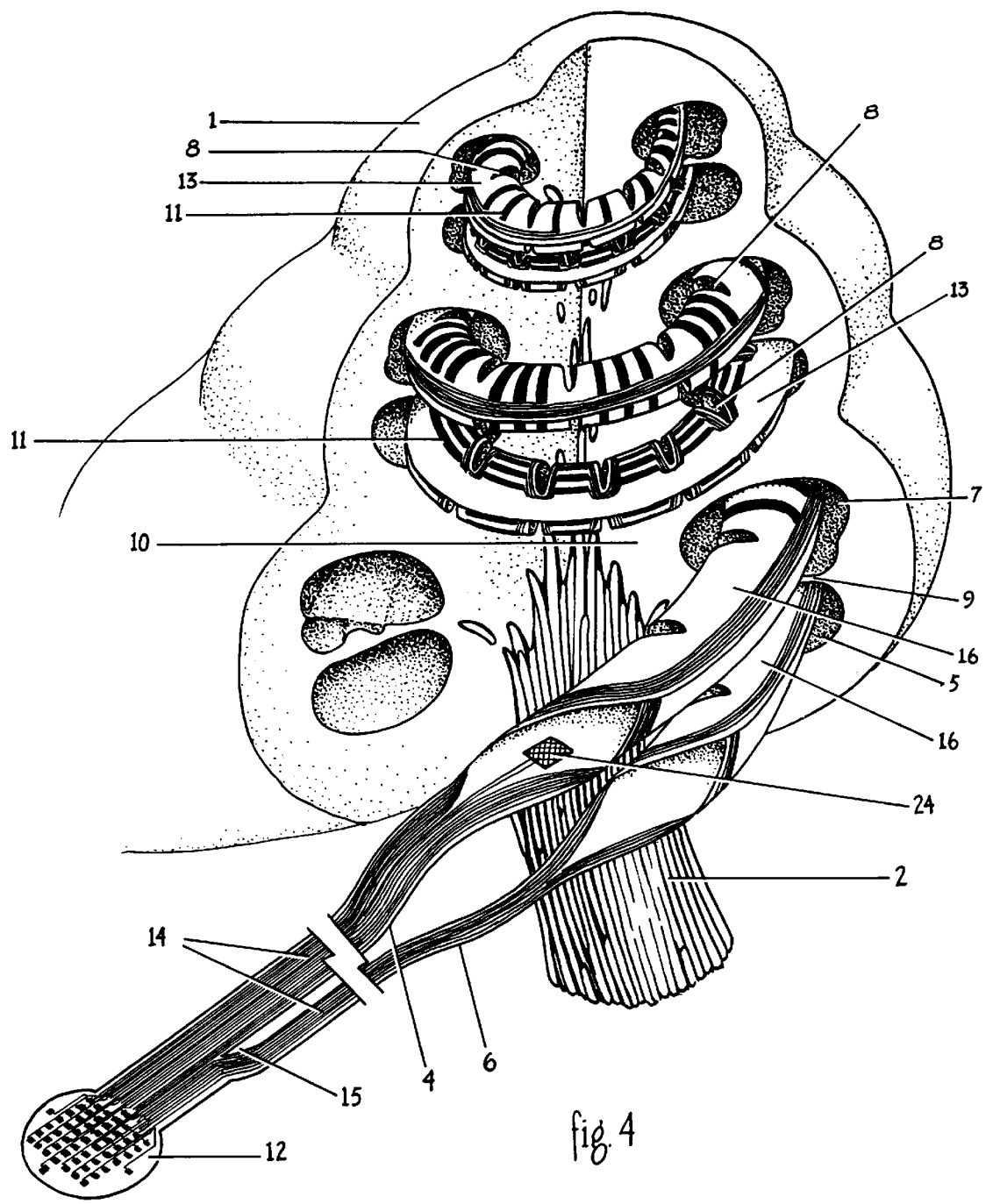
FIG. 4 is an enlarged cutaway, perspective view of the cochlea with the invention in place.

FIG. 1 is a cross sectional sketch of the scalae 1 showing all scalae, including the scala tympani 5 and the scala vestibuli 7. Referring to FIG. 1 and FIG. 4, the scalae are separated by the basilar membrane 9 which contains the nerves and hair cells 22 that are utilized by a person with healthy hearing to understand speech. It is these hair cells 22 that are typically inoperative or absent in a person with profound hearing loss. Both scalae are arranged in a spiral configuration consisting of approximately two and a half turns and rotating around the modiolus 10. The spiral ganglion cells 35 follow the turns of the cochlea and are generally present adjacent to the scala vestibuli 7 and the scala tympani 5. It is the residual functioning auditory processes in the basilar membrane 9 and the spiral ganglion cells 35 at the modiolus 10 that the invention proposes to stimulate.

Figure 2:
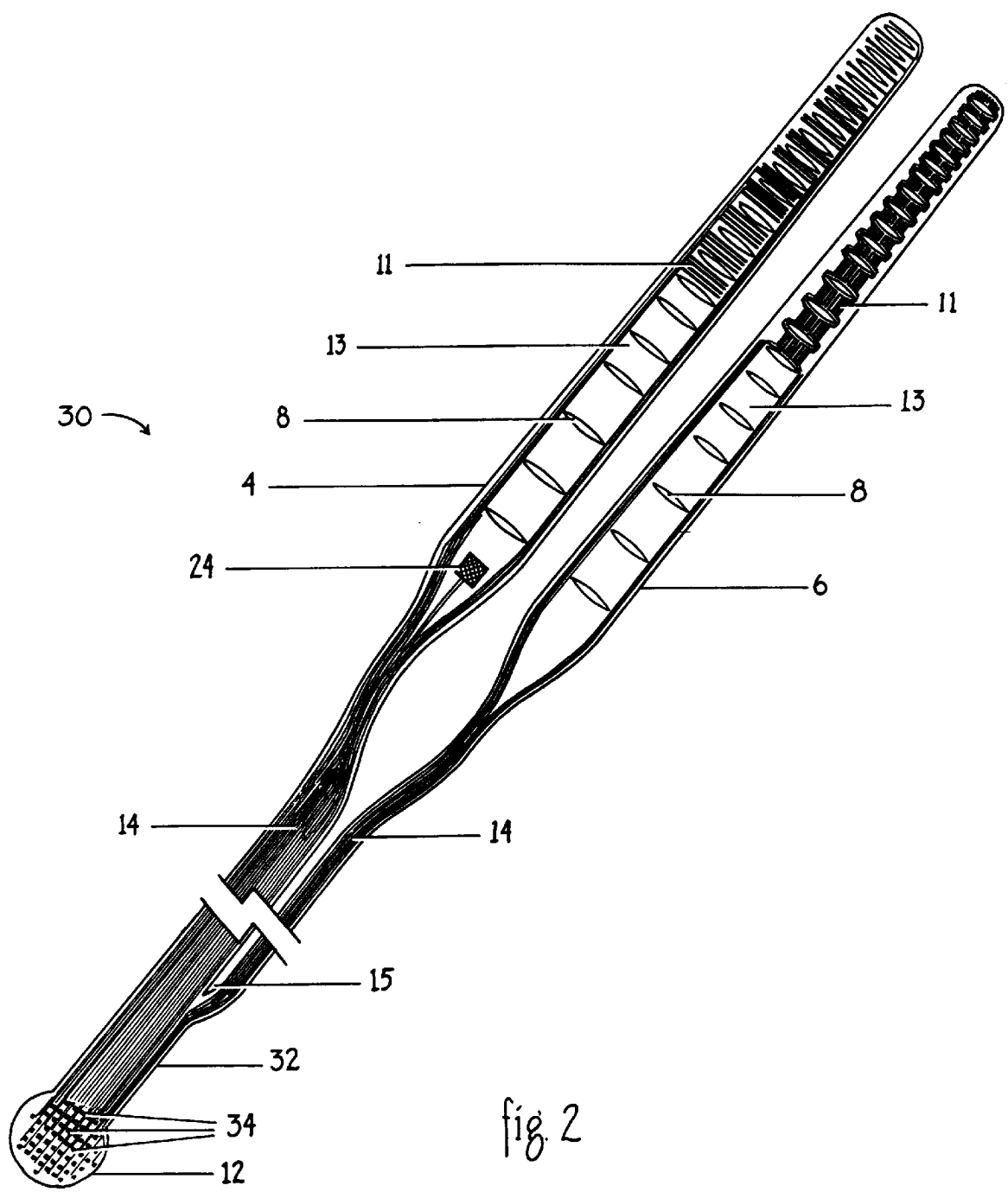
FIG. 2 is a plan view of the preferred embodiment of the implant according to the invention.

An implant device 30 according to the invention is illustrated in FIG. 2. The device 30 comprises two elongated and substantially flat prongs 4 and 6. Each prong 4 and 6 carries a plurality of electrodes 11. On prong 4, the electrodes 11 are oriented transversely to the longitudinal axis of the prong 4. On prong 6, the electrodes 11 are oriented longitudinally with respect to prong 6. It will be appreciated that the electrodes of prong 4 and 6 respectively are therefore orthogonal to one another.

Prongs 4 and 6 join at a common base 32. Base 32 includes a contact pad 12 which carries a plurality of terminations 34 for conductor lines 14 extending from each electrode 11 along the prong 4 or 6 to the contact pad 12. In the preferred embodiment, the common base 32 is approximately 5—5-mm long and 2–6 mm wide, the prongs 4 and 6 are each approximately 40–120 mm long and 2–6 mm wide.

FIG. 4 shows a cutaway, perspective view of the cochlea 1 and cochlear nerve 2 with the invention in place. Prong 6 is inserted in the scala tympani 5 and prong 4 is inserted in the scala vestibuli 7. Reissner's membrane 17, which separates the scala vestibuli and the scala media 18 as best seen in FIG. 1, is broken during this insertion. It is noted that the orthogonality between the electrodes 11 of both prongs is essentially preserved when the implant is in place in the scalae.

The preferred embodiment of the substrate for the implant consists of a thin planar, flexible, bio-compatible, non-conductive electrode-carrier such as silicone, polyimide, polyamide, polyethylene or a polyfuorocarbon which can be used as a support material for the metal electrodes 11, conductors 14 and contact pad 12. The electrodes 11 and conductors 14 which are joined near location 15 enable the surgeon to more easily implant one prong at a time and are preferably fabricated from a corrosion resistant metal such as platinum, rhodium, tantalum, or iridium or an alloy thereof. Additionally, a combination of two or more of these metals can be used, where one metal is electro or electroless plated or sputtered on the substrate metal. The electrode surface can also be coated with very thin dielectric coatings to allow said electrodes to be used capacitively. There are a number of methods whereby the metal component of the device can be fabricated by depositing the electrode metal on a non-conductive electrode-carrier, for example, CVD, sputtering, electroplating, electroless plating or by chemical etching of the appropriate metal foil. For example, M. Soon, et. al., in Medical and Biological Engineering, November 1974, pages 778–790, Pergamon Press, ISSN (0025-696X) describe a prototype flexible microelectrode array prosthesis for implantation using sputtered platinum onto a FEP Teflon (trademark) film substrate. G. A. May, et. al., IEEE Transactions on Electron Devices, Vol., Ed.-26, No. 12, December 1979 report the design of a tantalum-on-sapphire multielectrode array. More recently, van der Puije in U.S. Pat. No. 4,762,135 described a detailed fabrication process for making a planar electrode array that can be subsequently rolled up into a cylindrical shape, and which can be supported by an inner silicone core. Lupin in U.S. Pat. No. 5,344,387 teaches a method for wrapping a piezoelectric film on a tube. This technique can be extended by wrapping a flat lithographically fabricated foil on a similar tube or rod, or alternately, electrodes in a circular or longitudinal pattern can be sputtered, and then electro-plated, using a rotating cylindrical sputtering technology.

A microphone 24 is provided on or attached to prong 4 or prong 6. In the drawings, the microphone is illustrated as being attached to prong 4. The location of attachment of microphone 24 along the prong is chosen such that when the device 30 is implanted in the cochlea, the microphone will be located in or near the middle ear. It is advantageous to have the microphone, that is used to pick-up acoustic sounds for electronic processing and transmission to the electrodes in the cochlea, attached to, on or near to, the electrode-carrier substrate, at a location where the said substrate traverses the middle ear channel. This arrangement allows the patient to pick-up acoustic signals via the ear canal, thereby mimicking as close as possible the natural method of sound entering the ear. Conventional cochlear prostheses have the microphone located away from the external ear. In the preferred embodiment, the microphone 24 is positioned such that it will be located in the middle ear when the implant is in place. The microphone can be a discrete commercially available device, or it can be fabricated as an integral part of either prong 4 or 6, using for example, piezoelectric PVDF fluorocarbon film with platinum, rhodium, tantalum iridium, or alloys thereof, as the conductive element.

While FIG. 2 shows the preferred embodiment of the present invention where the electrodes 11 and conductor 14 are on the same side of the device surface, such embodiment is for manufacturing convenience only. An alternate embodiment is to provide electrodes 11 and conductors 14 positioned on opposing surfaces. In addition it is contemplated that each prong 4, 6 may be associated with its own separate contact pad as shown in FIG. 3a. In such case each contact pad is shaped as shown and are attached to a common substrate for subsequent connection with the processing unit. Other potential shapes for the contact pad are round, oval or square, for example, and such shapes do not depart from the scope of the invention.

Figure 3:
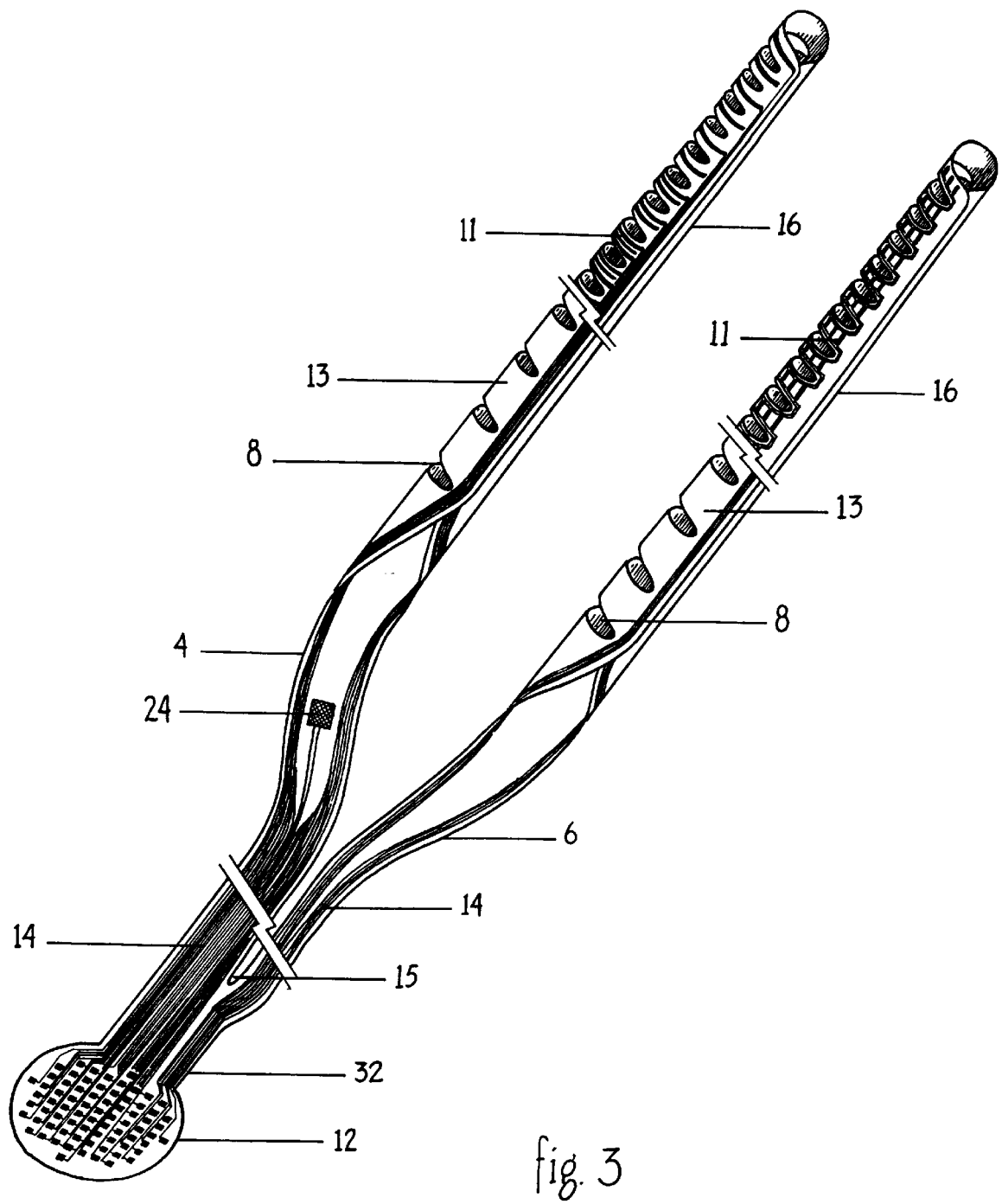
FIG. 3 is a perspective view of the invention with the two prongs rolled-up.
Figure 3A:
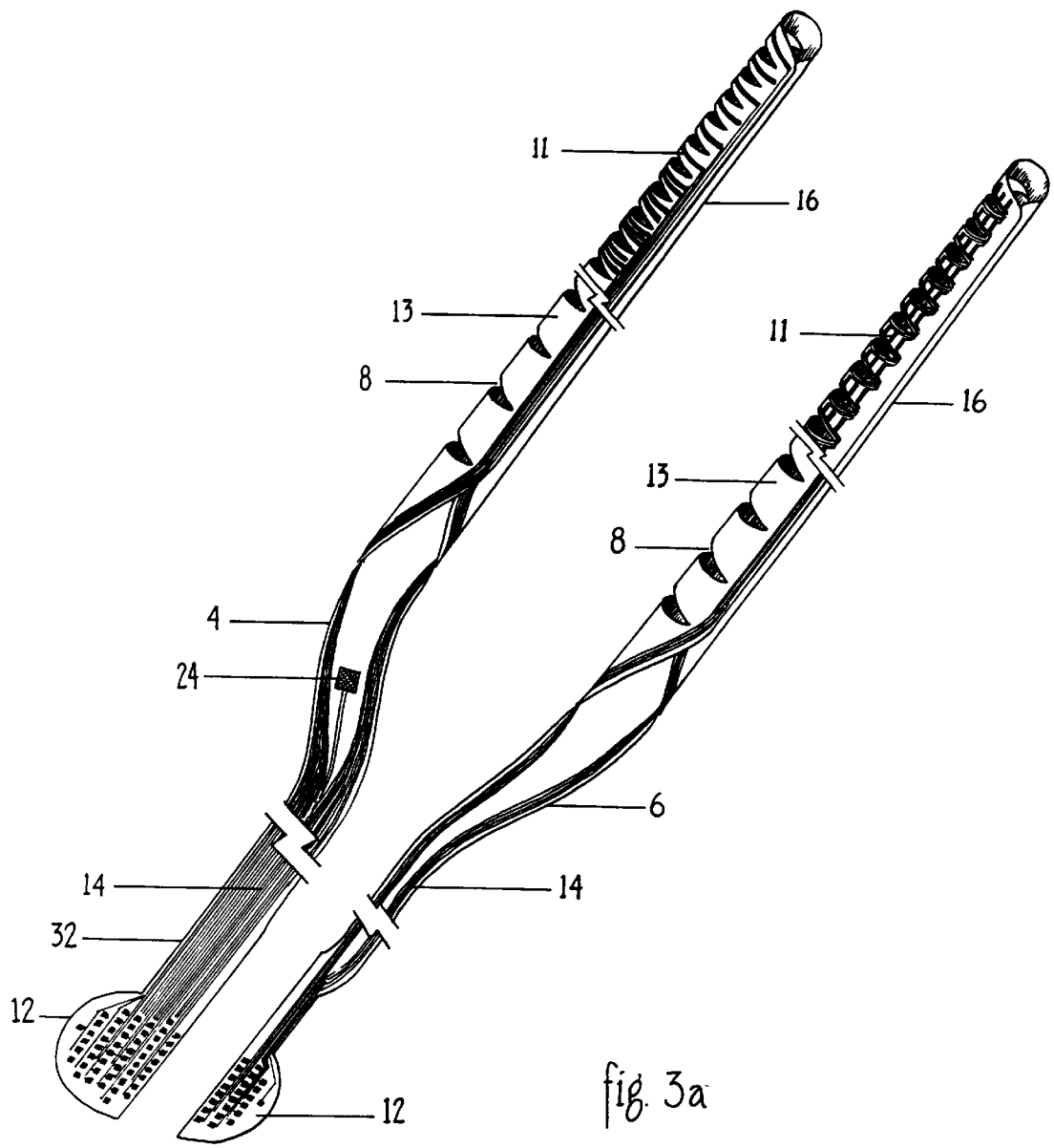
FIG. 3a is a perspective view of the invention showing the two separate prongs rolled up.

For insertion of the prongs 4, 6 into the scalae by a surgeon, each prong is separately rolled into a tube-like-like shape 16 whose outside diameter is less than about 0.7 mm (see FIG. 3). Note that the diameters of the scalae, which are somewhat elliptical, vary from about 2 mm near the basal end to less than 1 mm near the apical end (S. Hatsushika, et. al., Ann Otol Rhinol Laryngol 99:1990). The oval-like cut-outs 8 close as the rolled-up prongs bend during insertion, thereby minimizing kinking of the prongs. When prong 4 is rolled up, the electrodes 11 on prong 4 are disposed circumferentially on the prong.

In use, the output of the microphone 24 is transmitted to a processing unit (not shown) which may itself be an implant or may be externally mounted on the patient. The processing unit causes electrical impulses to be generated at specific points of the contact pad 12. Each of such points is associated with an electrode 11 and the processing unit is configured to select the points according to the optimum auditory perception in the patient. The correlation between the array of points on the contact pad 12 (or by extension the electrodes 11) and the auditory perception is established empirically through testing and initialization once the implant 30 is in place in the cochlea 1. As a result, only minimal circumferential orientation is required during surgical implantation since the choice of which sites to stimulate can be conveniently determined by inter-connecting the plurality of electrical contacts located on the contact pad 12.

A critical aspect for all electrodes that are implanted within the scala tympani (or scala vestibuli), is the ease of surgical insertability. The electrode array needs to be sufficiently rigid to allow insertion around the small tight bends of the cochlea, yet flexible and soft enough so as to not damage the delicate structures within the cochlea. Accordingly, most commercially successfully electrodes are fabricated of a soft inert electrode-carrier material such as silicone, with a cylindrical shape, a diameter of about 0.5 mm and smooth electrodes on the surface. Even then, full surgical insertion is difficult as noted by, for example by D. R. Ketten, et. al., in the abstract titled—In Vivo Measures of Intracochlear Electrode Position and Greenwood Frequency Approximations, in the 1997 Conference on Implantable Auditory Prostheses, Aug. 17–21, 1997 held in Pacific Grove, Calif., U.S.A.

To address this issue of surgical insertability of the prongs, the preferred embodiment of the invention shown in FIG. 3 includes small oval-like or elliptical-like shaped holes 8 cut out of the electrode-carrier substrate material to ease insertion of the rolled-up prongs into the scalae of the cochlea without kinking of the electrode-carrier material 13. The cut-outs 8 are oriented such that their longer axes are transverse to the longitudinal axis of the prongs. The cut-outs 8 allow the electrode-carrier substrate on the inside of the prong to close without buckling as the prong is inserted into the scala. In the case of the prong 6 with the longitudinally configured electrodes, some degree of circumferential orientation of the prong will be necessary during surgical insertion so that the electrodes are preferentially positioned towards the modiolus 10. This can be accomplished by having the oval-like prong cut-outs substantially face towards the modiolus 10 during surgical insertion, which orientation allows easier insertion into the scala in any case. The number of cut-outs will increase in density toward the proximal end as the cochlea decreases its rotational diameter around the modiolus 10. FIG. 3 shows the preferred device embodiment. For the prong 4 with the circumferentially configured electrodes 11, there can be about 4–12 cut-outs per one turn of the cochlea, with the width of an electrode set at approximately 10–300 microns depending upon the metal used in the electrode. For example, the use of iridium allows for use of smaller sizes than, say, platinum, due to differences in the surface chemistry of the metals exposed to the cochlea perilymph fluid.

The electrode material is constructed of malleable, biocompatible metal such that it can be circumferentially and longitudinally bent, and substantially retain its form upon bending, such that said electrodes will tend to retain their shape preferentially in the plane perpendicular to the length of the device prongs while remaining sufficiently rigid in the plane parallel to said prongs to allow for surgical insertion. The ability of a malleable metal to retain the rolled-up prong's form can be enhanced by adding extra metal to the prong, over that required simply for the electrodes and conductors. The tendency for the rolled-up prong to un-coil can be enhanced by using thicker and or stiffer non-conductive electrode carrier material such as FEP fluorocarbon, although this embodiment may require use of a tie-wrap or surgical thread wrapped around the outside diameter of the rolled-up prong as noted below.

Means to expand the rolled-up prongs of the present invention, in situ, can be conveniently accomplished using the natural spring effect of the prong's electrode material and or electrode-carrier material that will tend to un-coil, thus expanding the outside diameter of the rolled-up prong. This expansion means may be combined with, for example, the use of chemical expansion by hydroscopic core material present inside the rolled-up prong, which will gradually absorb fluid from the surrounding perilymph.

The number of electrodes 11 on prong 4 can be selected, for example, from only one to 25 or more, depending on the choice of electrode metal used, the degree of surface roughness of the metal (the use of a larger ratio of real surface to geometric surface allows for use of narrower electrode widths) and the degree of spatial resolution sought. One embodiment for prong 4 is to use platinum metal, with an electrode width of about 100 microns, spaced about 200 microns apart, which, for an insertion depth of about 25 millimeters (equivalent to about 17 millimeters along the modiolus wall 10), and with 10–15 cut-outs 8, allows for about 40 electrodes 11. The thickness of the electrodes 11 can be varied from about 0.2 micron to 200 micron, depending on the choice of the electrode spacing desired and the physical properties of the non-conducting electrode-carrier material 13 chosen, said material 13 which can be formed around the electrodes 11 by molding or thermoforming.

For the prong 6 with the longitudinally-configured electrodes, it is possible to use 1–12 or more electrodes. The choice of the number of electrodes will determine the electrode width and spacing between the electrodes. The use of more electrodes will increase the spatial resolution that is possible. As for the case of the prong 4 circumferentially-configured electrodes, the choice of the number of cut-outs 8 for the prong 6 longitudinally-configured electrodes can be varied from about 4–12 cut-outs per one turn of the cochlea 1. Accordingly, the width and separation between the prong 6 electrodes can vary. One embodiment is to use approximately 8–10 electrodes running substantially parallel to the length of the prong 6, arranged to be preferentially oriented towards the modiolus 10 after insertion into the scala (as illustrated in FIG. 4), with each electrode having a width of about 200 microns, and a separation of about 200 microns between electrodes.

One embodiment of fabricating the electrode array uses a process whereby 10–50 micron thick platinum foil is electro-chemically acid etched using a photolithographic process to pattern the areas to be etched, leaving a platinum pattern of electrodes 11, conductors lines 14, and contact pad 12. Said pattern is then sandwiched between two layers of a non-conductive electrode-carrier 13, each about 10–100 micron thick, where such carrier material 13 can be, for example, one of the polyflurocarbons, medical grade silicone, or polyethylene.

An alternative is to use platinum foil as the substrate material, which is then electro-plated with about 0.2 to 2 microns of iridium, and then coated or laminated with a carrier material 13 as per the above description. The iridium coating over the platinum substrate provides the advantages of the ductility of platinum for shaping the electrodes, the advantages of iridium for its exceptional corrosion resistance and surface chemistry properties (allowing for the use of much narrower widths of electrodes 11) than for example, only platinum. This embodiment has the potential of achieving in excess of 40 electrodes. Alternately, the electrodes could be constructed from an alloy of about 10% iridium and about 90% platinum, or of only iridium, although such designs would be more expensive, due to the higher cost of iridium, and stiffer, since iridium is not as ductile as platinum.

Since the orientation of the electrodes 11 on prong 6 provide only limited support of the rolled-up shape, one embodiment is to add additional ductile metal, such as platinum, on prong 6, that is not electrically functional, but acts to provide circumferential support to maintain the shape of the rolled-up prong 6.

In cases where the choice of the electrode-carrier material 13 is rigid, the use of mechanical means can be used to maintain the rolled-up shape. This can be accomplished by using, for example, a tie-wrap i.e. a narrow ribbon of polyfluorocarbon film, or surgical thread, which is wrapped around the outside of one or both rolled-up prongs 16 to maintain the rolled-up shape at a diameter smaller than the diameter of the scala, so that the prong can be inserted into the scala during the surgical implantation process, where such tie-wrap or thread is cut or loosened by the surgeon after implantation to allow the rolled-up prong 16 to expand closer to the scala wall surface 21 due to the natural spring effect of the rolled-up non-conductive electrode-carrier material or of the electrode material itself.

In cases where the choice of materials and electrode dimensions and number of electrodes is such that there is insufficient rigidity to insert either or both rolled up prongs 16, then one embodiment is to insert a thin flexible rod 36 or tube inside the rolled-up prongs 16, where such stiffening rod or tube can be removed or left in the cochlea 1 after surgical insertion of the prongs 16.

An embodiment of the thin flexible rod or tube is to shape the end of the rod to be rounded at the end first inserted into the cochlea, such rounded ends facilitating ease of insertion of prongs around sharp bends of the scalae. Also, such rounded ends can serve to substantially block the electrical connection via the conductive perilymph fluid between the scalae through the heliocotrema. Such blockage of the electrical conduction via the heliocotrema is important, since such a connection between the scala can act essentially as an electrical short, diverting electrical energy from one scala to the other, rather than through the basilar membrane or the spiral ganglion cells near the modiolus, which is the preferred path for stimulation of the nerve cells.

A further embodiment of the stiffening rod 36 is to use a rod that can also be used to see inside of the scala during insertion of a prong 16 by the surgeon, where such rod is made of substantially optically transparent material, such as glass or plastic, through which light can be transmitted and reflected light received, so that such rod acts to both stiffen the prongs 16 and to provide a convenient method to illuminate and view the inside of the scala.

Figure 5:
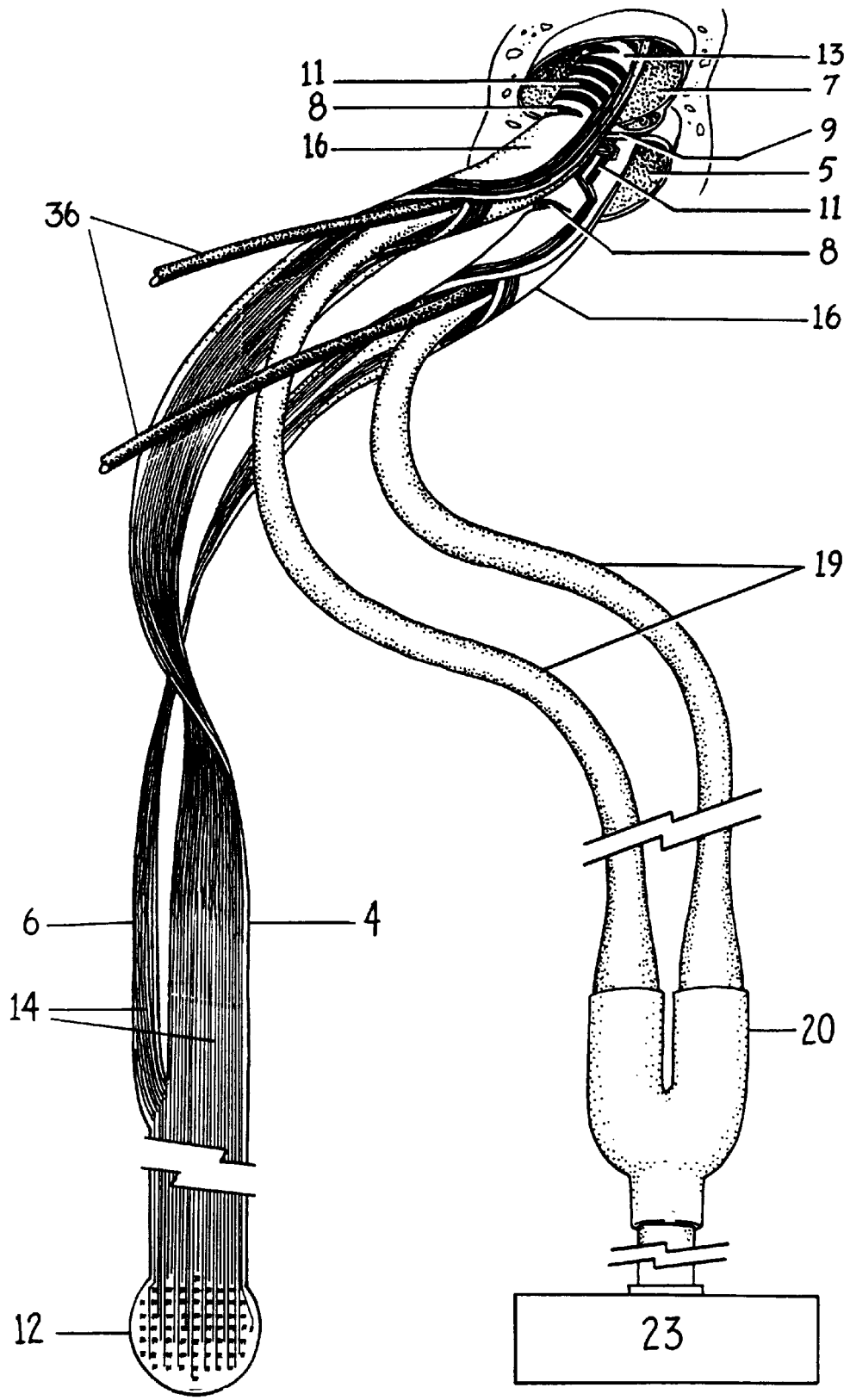
FIG. 5 is a perspective view of the invention partially inserted in the cochlea, in its unexpanded state, including a means for expansion of the prongs and a means to increase the rigidity of the rolled up prongs.

FIG. 5 illustrates both rolled-up prongs 4, 6 inserted into their respective scalae. Each prong is rolled around a thin-walled flexible tube 19, shown un-inflated, but which can be inflated using, for example, saline water. A coupler 20 ensures that equal pressure is provided in each thin-walled flexible tube 19 in each scala where such pressure can be provided by, for example, a syringe-like device 23, or any means for applying pressure to a fluid or gas in a controlled manner. The provision of equal pressure applied across the delicate basilar membrane 9 serves to minimize the possible rupture of this membrane. The use of the cut outs 8 allows the prongs to curve around the sharp bends within the cochlea without kinking the electrode-carrier (substrate) material.

Figure 7:
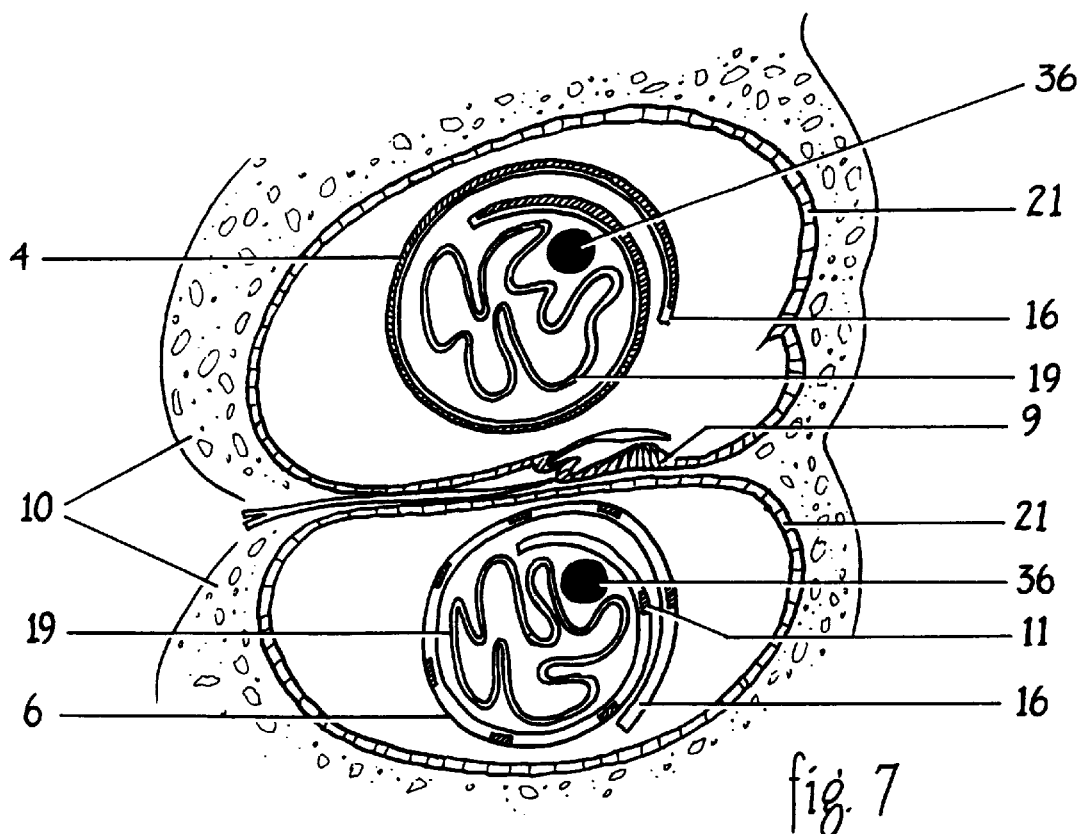
FIG. 7 is a cross sectional view of the invention partially inserted in the cochlea, in its unexpanded state, including a means for expansion of the prongs and a means to increase the rigidity of the rolled up prongs.

FIG. 7 illustrates a cross-sectional view of both rolled-up prongs 4, 6, inserted into their respective scalae prior to expansion of the tubes 19.

Figure 6:
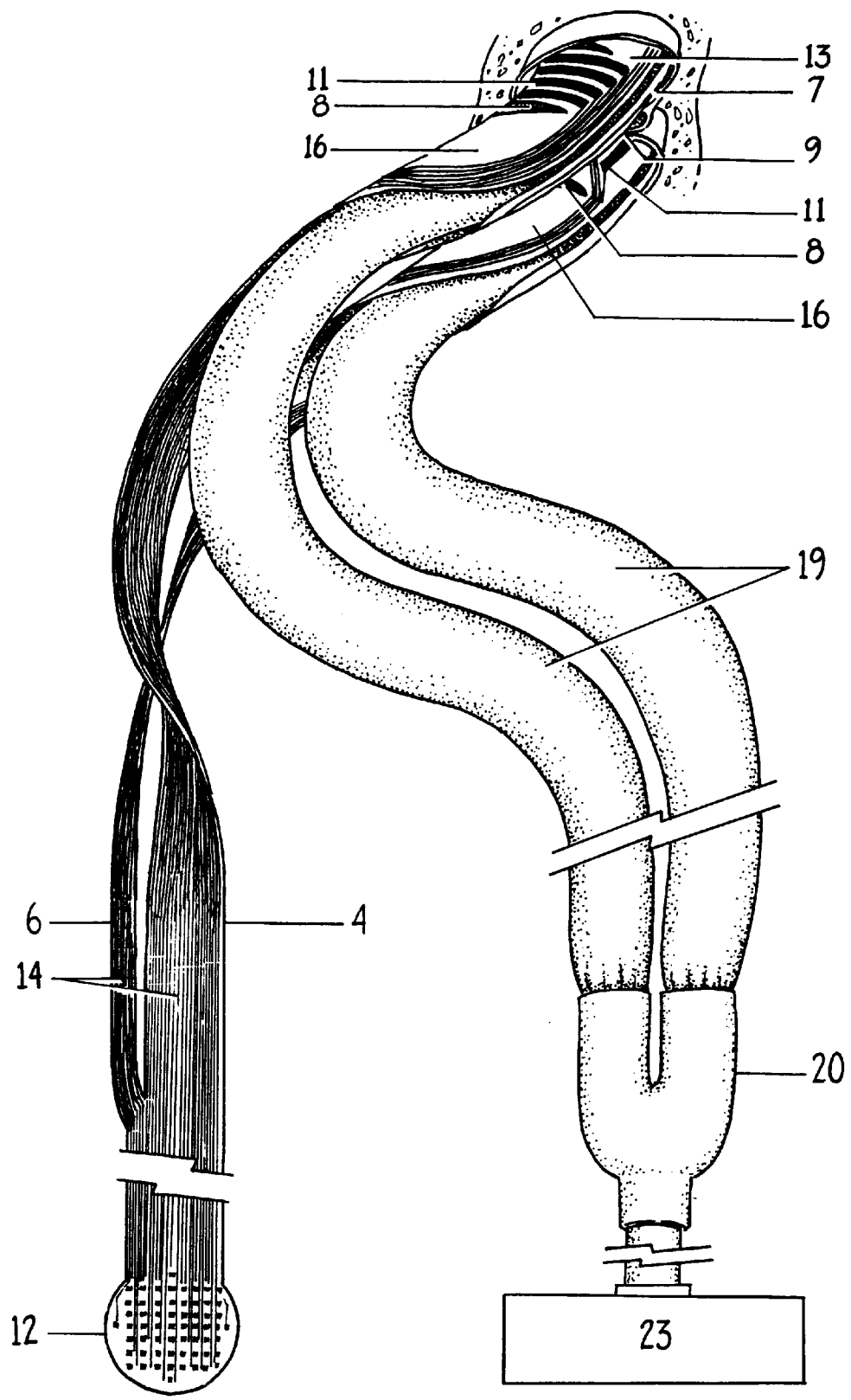
FIG. 6 is a perspective view of the rolled-up prongs after insertion in their respective scalae, with the expansion tube in its expanded state.

FIG. 6 shows a persrpective view of the rolled-up prongs seen in FIG. 5 with tubes 19 in their expanded state so as to urge the rolled-up prongs 4, 6 against the walls of the scalae. The use of a soft non-conductive electrode-carrier substrate, such as silicone or polytetrafluoroethylene (PTFE) allows the rolled-up electrodes and conductor lines to maintain a sufficiently small diameter necessary for surgical insertion. Also, in the absence of any oval-like cut outs in the prongs, the soft silicone or PTFE fluorocarbon material will allow some degree of buckling and kinking during surgical insertion and in situ expansion. The malleability of the platinum electrodes 11 and conductor lines 14 serves to permanently maintain the expanded shape of the rolled-up prongs, such that the prongs are touching or in close proximity to the scala walls. The thin-walled flexible tube 19, which can be made from, for example, thin-walled silicone, or thin-walled fluorocarbon tubing, can be removed after expansion by extracting the fluid and then pulling the tube out of the scalae, or, alternately, the thin-walled flexible tube 19 can be drained of fluid, and cut near the entry point into the cochlea, and left in the cochlea.

Figure 8:
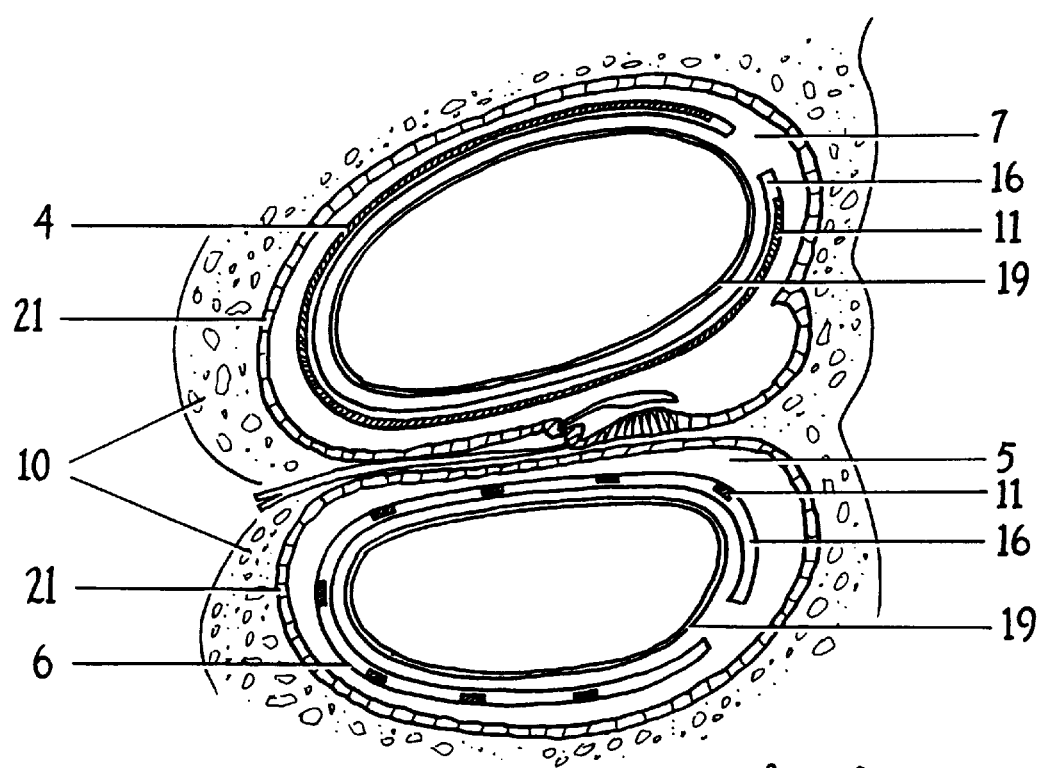
FIG. 8 is a cross sectional view of the rolled-up prongs after insertion in their respective scalae, with the expansion tube in its expanded state.

FIG. 8 illustrates a cross section of the expanded version of the rolled-up prongs 4, 6 positioned substantially against the walls of the scalae 5, 7.

Although either prong can be inserted into either scala, the preferred embodiment is to insert the circumferentially-configured prong 4 into the scala vestibuli 7, since, if ossification is present, it is likely to be greater in the scala tympani 5 (A. J. Gulya, et. al., Arch. Otolaryngo Head Neck Surg./Vol. 122, February 1996). If only one prong can be inserted due to ossification of one scala, the preferred embodiment is to insert only the prong 4 with circumferentially-configured electrodes into the other scala and simply cut away the prong 6 with longitudinally-configured electrodes. Thus, one embodiment of the invention is to use only one prong with circumferentially-configured electrodes that can be expanded in situ in the scala by inflating a thin-walled tube positioned inside the rolled-up prong. This embodiment will still provide a functional hearing device for the patient, albeit at some degradation in speech percepts by the patient.

The invention, once inserted, provides the means to stimulate the spiral ganglion cells 35 and the nerves adjacent to the basilar membrane 9 preferentially by directing the electric field from the scala vestibuli 7 to the scala tympani 5.

Other embodiments of electrode arrangements on a dual prong implant device are to (1) orient the electrodes circumferentially on both prongs, and (2) orient the electrodes circumferentially on one prong and use a single electrode on the other prong which covers the entire cylindrical surface area, said electrode essentially acting as a ground plane within the scala. Either of these electrode embodiments would still provide increased selectivity of stimulation sites and reasonable stimulation threshold currents compared to conventional bipolar and monopolar single prong electrode configurations.

The above description has been intended to illustrate the preferred and alternative embodiments of the invention. It will be appreciated that modifications and adaptations to such embodiments may be practised without departing from the scope of the invention, such scope being most properly defined by reference to this specification as a whole and to the following claims.

What is claimed is:

1. A cochlear implant for stimulating auditory processes comprising two elongated prongs extending from a common base, at least one contact pad on said base, one of said prongs being adapted to be implanted into the scala tympani and the other of said prongs being adapted to be implanted into the scala vestibuli, each of said prongs including at least one electrode, the electrodes on one of said prongs being oriented substantially orthogonally to the electrodes on the other of said prongs.

2. An implant according to claim 1 wherein the electrodes on one prong are oriented longitudinally on the prong while those on the other prong are oriented transversely to the longitudinal axis of the prong.

3. An implant according to claim 1 said at least one electrode being mounted on a non-conductive electrode-carrier substrate in the form of a planar strip, said strip being adapted to be rolled-up into a tube-like shape for implantation.

4. An implant according to claim 1 wherein, when each prong is rolled-up into a tube-like shape around the prong's longitudinal axis, the electrodes of one prong are oriented substantially circumferentially around the longitudinal axis of the prong and the electrodes of the other prong are oriented substantially parallel to the longitudinal axis of the prong.

5. An implant assembly comprising a cochlear implant for stimulating auditory processes including two elongated prongs joined at one end of a common base, at least one contact pad associated with said base, one of said prongs being adapted to be implanted in the scala tympani and the other of said prongs being adapted to be implanted in the scala vestibuli, each prong including at least one electrode mounted on a non-conductive electrode-carrier substrate in the form of a planar strip adapted to be rolled up into a tube-like configuration, wherein, when each prong is rolled-up into a tube-like shape around the prong's longitudinal axis, the electrodes of both prongs are oriented substantially circumferentially around the longitudinal axis and wherein each rolled up prong contains a thin-walled flexible expandable tube configured to expand one or both of said rolled up prongs when the tube is filled with a fluid or gas, thereby pushing the electrodes towards the scala wall surface.

6. An implant according to claim 3 wherein, when each prong is rolled-up into a tube-like shape around the prong's longitudinal axis, the electrodes of one prong are oriented substantially circumferentially around the longitudinal axis, while the electrodes of the other prong form a single continuous ground plane, acting substantially as a single electrode.

7. A cochlear implant for stimulating auditory processes, comprising two elongated prongs extending from a common base, at least one contact pad on said base, one of said prongs being adapted to be implanted into the scala tympani and the other of said prongs being adapted to be implanted into the scala vestibuli, each of said prongs including at least one electrode, wherein said electrodes comprise a malleable, bio-compatible, metal such that it can be circumferentially and longitudinally bent, and substantially retain its form upon bending such that said electrodes will tend to retain their shape preferentially in the plane perpendicular to the length of the prongs while remaining sufficiently rigid in the plane parallel to said prongs to allow for surgical insertion, and wherein the electrodes on one of said prongs are oriented substantially orthogonally to the electrodes on the other of said prongs.

8. An implant according to claim 2, which contains at least 25 electrodes on the prong with the transversely configured electrodes, and at least 1 electrode on the prong with the longitudinally configured electrodes.

9. An implant according to claim 2, which contains at least 25 electrodes on the prong with the transversely configured electrodes, and at least 4 electrodes on the prong with the longitudinally configured electrodes.

10. An implant assembly comprising a cochlear implant for stimulating auditory processes including two elongated prongs joined at one end of a common base, one of said prongs being adapted to be implanted in the scala tympani and the other of said prongs being adapted to be implanted in the scala vestibuli, at least one contact pad associated with said base, each prong including at least one electrode mounted on a non-conductive electrode-carrier substrate rolled up about its longitudinal axis, each rolled up prong containing a thin-walled flexible expandable tube configured to expand one or both of said rolled up prongs when the tube is filled with a fluid or gas, thereby pushing the electrodes towards the scala wall surface and wherein the electrodes of both rolled up prongs are oriented substantially circumferentially about the longitudinal axes of the prongs.

11. An implant assembly according to claim 10, wherein the thin-walled tube is made from silicone or a fluorocarbon material.

12. A cochlear implant assembly for stimulating auditory processes comprising an implant having a single elongated prong, a plurality of electrodes mounted or formed on said prong, wherein said implant is rolled up about the prong's longitudinal axis around a flexible and expandable thin-walled tube configured to expand said rolled up prong when the tube is filled with a fluid or gas, thereby pushing the electrodes towards the scala wall surface.

13. An implant assembly according to claim 12, wherein the thin-walled tube is made from silicone or a fluorocarbon material.

14. An implant assembly according to claim 10, wherein said fluid is a saline solution.

15. An implant assembly according to claim 10 wherein said fluid is a low viscosity substance or medical grade silicone that will harden somewhat over time.

16. An implant assembly according to claim 12 wherein said fluid is a saline solution.

17. An implant assembly according to claim 10 further comprising means for expanding the thin-walled tube at substantially the same pressure in both prongs so as to protect the basilar membrane from undue pressure and possible rupture.

18. An implant assembly according to claim 10 further comprising a flexible support rod or tube inside at least one of the rolled-up prong so as to increase the rigidity of either said rolled-up prong to aid implantation into the scala.

19. An implant assembly comprising a cochlear implant for stimulating auditory processes including two elongated prongs joined at one end of a common base, one of said prongs being adapted to be implanted in the scala tympani and the other of said prongs being adapted to be implanted in the scala vestibuli, at least one contact pad associated with said base, each prong including at least one electrode mounted on a non-conductive electrode-carrier substrate in the form of a planar strip rolled up into a tube-like configuration, and further comprising a tie wrap or surgical thread wrapped around the outside of one or both rolled-up prongs to maintain the rolled-up shape at a diameter smaller than the diameter of the scala, so that the prong can be inserted into the scala during the implantation process, wherein said tie wrap or surgical thread is adapted to be loosened by the surgeon after implantation and wherein said substrate or electrodes have a natural spring effect tending to unroll said prongs and wherein the electrodes on one of said prongs are oriented substantially orthogonally to the electrodes on the other of said prongs.

20. An implant according to claim 3, further comprising extra malleable metal, adapted to maintain the prongs in a rolled-up shape during and after implantation and to maintain the prongs in an expanded state after implantation.

21. An implant according to claim 1 wherein spaced elliptical-like cut outs are provided on said prongs so as to minimize kinking of the prong during insertion.

22. An implant assembly according to claim 18, wherein said rod is made of substantially optically transparent material, such as glass or plastic, to allow light to be transmitted down the rod, and to allow reflected light to be received from inside the scala, such that the surgeon can view the inside of the scala during surgical insertion of a prong.

23. An implant assembly according to claim 18 wherein said rod or tube is rounded at the end first inserted into the cochlea to allow for ease of insertion of the prongs into the sharp bends of the scalae, and to reduce the electrical conductivity between the scalae via the heliocotrema, by substantially blocking the passage connecting the scalae.

24. A method of surgically implanting an implant according to claim 1 wherein one of said prongs is implanted into the scala tympani and the other of said prongs is implanted into the scala vestibuli.

25. An implant assembly comprising a cochlear implant for stimulating auditory processes including two elongated prongs joined at one end of a common base, at least one contact pad associated with said base, one of said prongs being adapted to be implanted in the scala tympani and the other of said prongs being adapted to be implanted in the scala vestibuli, each prong including at least one electrode mounted on a non-conductive electrode-carrier substrate in the form of a planar strip adapted to be rolled up into a tube-like configuration, wherein, when each prong is rolled-up into a tube-like shape around the prong's longitudinal axis, the electrodes of both prongs are oriented substantially circumferentially around the longitudinal axis and wherein each rolled up prong contains a thin-walled flexible expandable tube configured to expand one or both of said rolled up prongs when the tube is filled with a fluid or gas, thereby pushing the electrodes towards the scala wall surface and wherein said electrodes comprise a malleable, bio-compatible, metal such that it can be circumferentially and longitudinally bent, and substantially retain its form upon bending, such that said electrodes will tend to retain their shape preferentially in the plane perpendicular to the length of the prongs while remaining sufficiently rigid in the plane parallel to said prongs to allow for surgical insertion.

26. An implant assembly comprising a cochlear implant for stimulating auditory processes including two elongated prongs joined at one end of a common base, one of said prongs being adapted to be implanted in the scala tympani and the other of said prongs being adapted to be implanted in the scala vestibuli, at least one contact pad associated with said base, each prong including at least one electrode mounted on a non-conductive electrode-carrier substrate rolled up about its longitudinal axis, each rolled up prong containing a thin-walled flexible expandable tube configured to expand one or both of said rolled up prongs when the tube is filled with a fluid or gas, thereby pushing the electrodes towards the scala wall surface and wherein the electrodes of both rolled up prongs are oriented substantially circumferentially about the longitudinal axes of the prongs, and wherein the electrodes on one of said prongs are oriented substantially orthogonally to the electrodes on the other of said prongs.

27. An implant assembly comprising a cochlear implant for stimulating auditory processes including two elongated prongs joined at one end of a common base, one of said prongs being adapted to be implanted in the scala tympani and the other of said prongs being adapted to be implanted in the scala vestibuli, at least one contact pad associated with said base, each prong including at least one electrode mounted on a non-conductive electrode-carrier substrate in the form of a planar strip rolled up into a tube-like configuration, and further comprising a tie wrap or surgical thread wrapped around the outside of one or both rolled-up prongs to maintain the rolled-up shape at a diameter smaller than the diameter of the scala, so that the prong can be inserted into the scala during the implantation process, wherein said tie wrap or surgical thread is adapted to be loosened by the surgeon after implantation and wherein said substrate or electrodes have a natural spring effect tending to unroll said prongs and wherein the electrodes on one of said prongs are oriented substantially orthogonally to the electrodes on the other of said prongs and wherein said electrodes comprise a malleable, bio-compatible, metal such that it can be circumferentially and longitudinally bent, and substantially retain its form upon bending, such that said electrodes will tend to retain their shape preferentially in the plane perpendicular to the length of the prongs while remaining sufficiently rigid in the plane parallel to said prongs to allow for surgical insertion.

* * * * *